United States Patent
Wang et al.

(10) Patent No.: US 7,303,887 B2
(45) Date of Patent: Dec. 4, 2007

(54) MULE: MCL-1 UBIQUITINATION LIGASE E3

(75) Inventors: Xiaodong Wang, Dallas, TX (US); Qing Zhong, Dallas, TX (US); Wenhua Gao, Dallas, TX (US); Fenghe Du, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 131 days.

(21) Appl. No.: 11/132,977

(22) Filed: May 18, 2005

(65) Prior Publication Data

US 2006/0264366 A1    Nov. 23, 2006

(51) Int. Cl.
*G01N 33/53*  (2006.01)
*C07K 5/10*  (2006.01)

(52) U.S. Cl. ...................................... 435/7.1

(58) Field of Classification Search ............... None
See application file for complete search history.

(56) References Cited

OTHER PUBLICATIONS

Nandi et al J Biosci, 2006, 31:137-155.*
World wide web.ncbi.nlm.nih.gov/entrez/query.fcgi?CMD=search&DB=protein (Mule E3 ubiquitin ligase).*

* cited by examiner

*Primary Examiner*—Misook Yu
*Assistant Examiner*—Mark Halvorson
(74) *Attorney, Agent, or Firm*—Richard Aron Osman

(57) ABSTRACT

A HECT-domain containing E3 ubiquitin ligase that mediates the polyubiquitination of Mcl-1, named Mule for Mcl-1 ubiquitin ligase E3, is described. Methods and compositions for modulating functional interaction between Mcl-1 and Mule protein and Mcl-1 mediated apoptosis are described. Diagnostic and prognostic methods based on Mule expression in patient cells are also described.

18 Claims, No Drawings

MULE: MCL-1 UBIQUITINATION LIGASE E3

This work was supported by National Institute of Health Grant GMRO1-57158. The U.S. government may have rights in any patent issuing on this application.

FIELD OF THE INVENTION

The field of the invention is a Mcl-1 ubiquitin ligase E3 and methods of use.

BACKGROUND OF THE INVENTION

Apoptosis is a form of cell death orchestrated by chains of biochemical reactions. Cells undergoing apoptosis show characteristic morphological features such as condensation of cytoplasmic and nuclear contents, blebbing of plasma membranes, fragmentation of nuclei, and ultimately breakdown into membrane-bound apoptotic bodies that are rapidly phagocytosed (Kerr et al., 1972).

Mitochondria play an important role in regulating apoptosis induced by intracellular damaging signals such as DNA damage in mammalian cells (Danial and Korsmeyer, 2004). Apoptotic stimuli exert their effects on mitochondria to cause the release of pro-apoptotic factors like cytochrome c and Smac/Diablo. These factors either directly activate caspases, a group of intracellular cysteine proteases that execute apoptosis by cleaving their substrates, or release caspase-inhibition imposed by the inhibitor of apoptosis proteins (IAPs) (Du et al., 2000; Liu et al., 1996; Verhagen et al., 2000).

Mitochondrial response to apoptotic stimuli is regulated by the pro- and anti-apoptotic Bcl-2 family of proteins (Gross et al., 1999; Martinou and Green, 2001). Anti-apoptotic proteins such as Bcl-2, Bcl-xL, and Mcl-1 protect mitochondrial integrity, while the pro-apoptotic members of the family promote the release of apoptogenic proteins from mitochondria. The fate of a cell under apoptotic stimulation is determined by the balance of the function between the pro- and anti-apoptotic members of Bcl-2 family. Therefore, studying the upstream regulation of Bcl-2 family proteins will be critically important for our understanding of apoptosis regulation.

Among the anti-apoptotic members of the Bcl-2 family proteins, Mcl-1 is unique in that it is an early-response gene that can be rapidly induced and turned over (Kozopas et al., 1993; Yang et al., 1996; Yang et al., 1995). This property enables Mcl-1 to function at an apical step in a signaling cascade consisting of Bcl-2 family proteins and provides an acute protective function against apoptosis induced by a variety of stimuli including DNA damage, adenoviral infection, growth factors withdrawal and treatment of cytotoxic agents (Cuconati et al., 2003; Derouet et al., 2004; Huang et al., 2000; Le Gouill et al., 2004; Nijhawan et al., 2003; Piret et al., 2004; Zhang et al., 2002; Zhou et al., 1998; Zhou et al., 1997). Consistently, disappearance of Mcl-1 is associated with the onset of apoptosis and is achieved by the combination of synthesis blockage and continuous degradation (Cuconati et al., 2003; Nijhawan et al., 2003).

The degradation of Mcl-1 in HeLa cells can be blocked by proteasome inhibitors, suggesting a role for the ubiquitin proteasome pathway in apoptosis upstream of Bcl-2 family of proteins (Derouet et al., 2004; Nencioni et al., 2004; Cuconati et al., 2003; Nijhawan et al., 2003). Here, we identify an E3 ubiquitin ligase that mediates the polyubiquitination of Mcl-1. This protein is a novel HECT-domain containing ubiquitin ligase, which we named Mule for Mcl-1 ubiquitin ligase E3. Mule is the first E3 ligase specifically identified that regulates the Bcl-2 family of proteins. The carboxy 308 amino acids of human Mule are identical to a protein previously identified as a 308 amino acid named UREB1 for "upstream regulatory element binding protein 1" (Gu et al, 1994; GenBank ID 3694922); and amino acids 1055-4374 of Mule are identical to amino acids 40-3360 of gi: 22090626, which entered GenBank August, 2002, and is named LASU1 for large structure of UREB1.

We made a presentation at the 2003 Cold Spring Harbor meeting on programmed cell death about the identification and purification of Mule without revealing its identity other than its name and that it was a large, HECT-domain containing protein (Meier P., Silke J., 2003).

Subsequent to our identification of Mule, the same protein was reported as functioning as an E3 enzyme that ubiquitinates histones in spermatids during spermatogenesis (Liu et al, 2005). The human and mouse Mule polypeptide sequences are listed in GenBank as gi:61676188 (accession no. NP_113584.3) and gi:61676190 (accession no. NP_067498.3), respectively, and the corresponding nucleotide sequences are gi:61676187 (accession no. NM_031407.3) and 61676189 (accession no. NM_21523), respectively.

SUMMARY OF THE INVENTION

The invention provides methods and compositions for modulating the functional interaction between Mcl-1 and a Mule protein. In one embodiment, the invention provides methods for identifying an agent that modulates binding of Mcl-1 with a Mule polypeptide comprising a Mule BH3 domain in a mixture, comprising contacting the mixture with a candidate agent under conditions wherein but for the presence of the agent, the Mcl-1 and Mule polypeptide engage in a reference binding; and specifically detecting an agent-biased binding of the Mcl-1 and Mule polypeptide; wherein a difference between the reference and agent-biased bindings indicates that the agent is a modulator of binding of the Mcl-1 and the Mule polypeptide.

In particular embodiments, the Mcl-1 and Mule polypeptide are isolated, recombinantly-expressed, or in a predetermined amount.

In particular embodiments, the mixture is within a cell transformed to express the Mcl-1 or the Mule polypeptide. Alternatively, the mixture may be cell-free.

In particular embodiments, the agent-biased binding is detected in an in vitro Mcl-1 ubiquitination assay, a co-immunoprecipitation assay, or in a solid phase binding assay. In one embodiment, the agent-biased binding is detected in a solid phase binding assay and the Mule polypeptide consists essentially of a human Mule BH3 domain peptide.

In one embodiment, the method further comprises a step of testing the agent in an apoptosis assay, and detecting a reduction or increase in apoptosis caused by the agent.

Another aspect of the invention is a method of characterizing a cancer cell of a patient, the method comprising the step of: determining Mule expression in a cancer cell from the patient, wherein reduced or non-reduced Mule expression relative to that of a control cell indicates that the cancer cell is resistant to or amendable to, respectively, a Mule-dependent therapy; and correspondingly characterizing the cancer cell as resistant to or amenable to a Mule-dependent therapy, wherein the Mule dependent therapy is a DNA damaging therapy.

In particular embodiments the DNA damaging therapy is selected from UV-irradiation, etoposide and cisplatin.

In one embodiment, the determining step is effected by: contacting a fraction of the cancer cell with a Mule-specific binding reagent selected from a Mcl-1 polypeptide or antibody that specifically binds Mule; and measuring specific binding of the reagent to Mule, to provide an indication of Mule expression in the cancer cell. In a further embodiment, the Mule is and immobilized.

In another embodiment, the determining step is effected by: contacting a fraction of the cancer cell with a Mule mRNA sequence specific probe; and measuring specific hybridization of the probe to Mule mRNA or corresponding cDNA, to provide an indication of Mule expression in the cancer cell.

Another aspect of the invention is a method of detecting reduced Mule expression in a cancer cell, the method comprising: contacting a fraction of the cell with a Mule-specific binding reagent; and detecting a reduction in reagent-bound Mule relative to a control, wherein a reduction in reagent-bound Mule relative to control indicates that the cell has reduced Mule expression, wherein the reagent is selected from a Mcl-1 polypeptide or antibody that specifically binds Mule. In one embodiment, the method further comprises a step of contraindicating a Mule-dependent therapy, wherein the Mule dependent therapy is a DNA damaging therapy selected from the group consisting of UV-irradiation, etoposide and cisplatin.

The invention also provides an isolated Mule protein and an isolated peptide comprising a human or mouse Mule BH3 domain wherein the peptide lacks a HECT domain and blocks ubiquitination of Mcl-1 by Mule. Recombinant nucleic acids encoding the Mule protein or peptide are also provided.

Another aspect of the invention is a method of inhibiting Mule interaction with Mcl-1 in a Mule- and Mcl-1-expressing cell, by reducing functional expression of Mule or blocking the interaction of Mule and the Mcl-1 in the cell, by: contacting the cell with a Mule-specific reagent selected from siRNA, PNA, morpholino, antisense RNA, intrabody, and a Mule BH3 domain peptide.

In a particular embodiment, the cell is in a patient, and the method comprises an antecedent step of detecting in the patient a pathology of apoptosis.

In another embodiment, the method comprises a subsequent step of detecting in the cell a resultant inhibition of Mcl-1-mediated apoptosis.

The invention also provides a method of identifying a Mule allele as being associated with increased risk of a disease or disorder of pathological apoptosis, the method comprising the step of: detecting the presence of a same Mule allele in a plurality of persons with a disease or disorder of pathological apoptosis, wherein the selective presence of the allele in these persons identifies the allele as being associated with increased risk of a disease or disorder of pathological apoptosis. In a particular embodiment, the disease or disorder is a cisplatin-resistant cancer.

DETAILED DESCRIPTION OF SPECIFIC EMBODIMENTS OF THE INVENTION

The invention provides methods and compositions for modulating the functional interaction between Mcl-1 and a Mule protein.

In one aspect, the invention provides an isolated Mule protein. Referring to amino acid (aa) numbering of the human and mouse proteins (gi:61676188, and gi:61676190, respectively), Mule proteins are characterized by the following domains: two domains resembling ARM (Armadillo) like repeats which we named ARLD1 (Arm Repeat-Like Domain 1; aa 104-374) and ARLD2 (aa 424-815); a ubiquitin-associated (UBA) domain (aa 1317-1355); a WWE domain (see e.g. Aravind, 2001; Hofmann and Bucher, 1996) in the middle of the protein (aa 1617-1678); a BH3 domain (aa 1972-1994), which we show interacts with Mcl-1; and a COOH-terminal HECT (Homology to the E6-AP Carboxyl Terminus) ubiquitin ligase domain (human aa 4016-4374; mouse aa 4020-4378). Mule is highly conserved in mammals. Unless indicated otherwise, further Mule amino acid residue numbering mentioned herein will be in reference to human Mule (gi:61676188); and Mcl-1 amino acid residue numbering corresponds to human Mcl-1, isoform 1 (GenBank accession no. NP-068779; gi:11386165).

The isolated Mule protein can be obtained by purification of the native protein (see Example 3) or by recombinant expression (see Example 4). A Mule protein can be optionally expressed as a fusion protein, for example with a peptide label such as FLAG to facilitate purification, a marker such as GFP, etc. The invention also provides a recombinant nucleic acid encoding a Mule protein, and a cell comprising the recombinant nucleic acid. Both Mcl-1 and Mule are well-conserved in animals as documented in publicly available sequences databases, such as Genbank. Accordingly, in addition to preferred human or mouse varieties, the subject methods and compositions encompass proteins from alternative species, such as other mammalian species such as canine, bovine, primate, rat, etc.

Another aspect of the invention is an isolated peptide comprising a human or mouse Mule BH3 domain, wherein the peptide lacks a HECT domain and blocks ubiquitination of Mcl-1 by Mule. We show that Mule is a novel member of the "BH3 only" family proteins. Members of the Bcl-2 family of proteins containing only BH3 domain use this domain to interact with other family members. We show that Mule uses its BH3 domain to interact with Mcl-1, and that a peptide containing this domain (aa 1969-1994) competes for Mule-Mcl-1 interaction therefore blocking Mcl-1 ubiquitination (see Example 5). The peptide can comprise any BH3-domain-containing portion of a HECT-domain truncated Mule (e.g. aa 1-4015). In particular embodiments, the peptide comprises less than 1000, 500, 100, or 50 amino acid residues. In one embodiment, the peptide consists essentially of amino acids 1972-1994 of human or mouse Mule.

Another aspect of the invention is an antibody that binds a peptide consisting of amino acids 1972-1994 of Mule. In particular embodiments, the antibody is monoclonal, humanized, or is an intrabody. Additional aspects of the invention are a recombinant nucleic acid encoding the peptide, and a cell comprising the recombinant nucleic acid.

The invention further provides a method for identifying an agent that modulates binding of Mcl-1 with a Mule polypeptide comprising a Mule BH3 domain in a mixture, comprising contacting the mixture with a candidate agent under conditions wherein but for the presence of the agent, the Mcl-1 and the Mule polypeptide engage in a reference binding; and specifically detecting an agent-biased binding of the Mcl-1 and Mule polypeptide; wherein a difference between the reference and agent-biased bindings indicates that the agent is a modulator of binding of the Mcl-1 and the Mule polypeptide.

The mixture that contains the Mcl-1 and Mule polypeptide can be in a cell in vitro or in situ, in a cell-fraction or lysate, or essentially cell-free. In certain embodiments using cell-based methods, a mammalian, preferably human, tumor cell line is used (e.g. HeLa, U20S, etc.). In a cell-based assay, the cell may endogenously express the Mcl-1 and/or the Mule polypeptide, or it may be transformed to express the Mcl-1 and/or the Mule polypeptide. In a cell-free assay, the Mcl-1 and Mule polypeptide can be isolated and/or in a predetermined amount.

The candidate agent can be from any class of compound or molecule that is tested for therapeutic effect. In particular embodiments, the candidate agent is selected from small molecules, small interfering RNA (siRNA), peptide nucleic acid (PNA), morpholino, antisense RNA, intrabodies, and peptides.

Any assay format that can specifically detect agent-biased binding of Mcl-1 and Mule and thus provides a quantitative or qualitative measure of Mcl-1/Mule binding can be used. Suitable assay formats for testing candidate agents are routinely selected by the skilled artisan. In particular embodiments, the agent-biased binding is specifically detected in an in vitro Mcl-1 ubiquitination assay, a co-immunoprecipitation assay, or a solid-phase binding assay.

In an exemplary in vitro Mcl-1 ubiquitination assay, recombinant human Mcl-1 is incubated with an ATP regenerating system (see Example 2), Methyl-ubiquitin, recombinant human E1, human E2 (e.g. Ubch7), ubiquitin aldehyde, and recombinant Mule or a Mule-containing cell fraction (e.g. Hela cell S100 fraction) with and without the candidate modulating agent. Reaction products are fractionated by a biochemical/electrophoretic gel based-assay that measures Mcl-1 protein mobility shifts (mass shift). Mass spectrometry analysis may also be used to quickly define the presence or absence of the ubiquitination. Because functional Mule is specifically required for Mcl-1 ubiquitination, increased or decreased ubiquitination in the presence of the candidate agent provides a specific indication of Mcl-1/Mule binding.

In another embodiment, a co-immunoprecipitation assay is used to specifically detect agent-biased binding of the Mcl-1 and Mule polypeptide. In an exemplary assay, HeLa cells stably expressing Flag-tagged Mcl-1 are treated with and without the candidate modulating agent. Cells are lysed and cell extracts are immunoprecipitated by anti-Flag mAb. The immunoprecipitate is subjected to SDS-PAGE followed by electroblotting to a nitrocellulose filter. The filter is probed with an anti-Mule antibody and exposed to an X-ray film.

Agent-biased binding can also be specifically detected in a solid phase binding assay. With a solid-phase binding assay the Mule polypeptide may be bound to a solid-phase, and the amount of a labeled (e.g. biotinylated, radiolabeled, antibody-labeled etc.) Mcl-1 that binds to Mule in the presence and absence of the candidate agent is detected. Alternatively, the Mcl-1 may be bound to the solid phase, and the amount of a labeled Mule polypeptide that binds to the Mcl-1 in the presence and absence of the agent is detected. Such solid-phase assays are particularly amenable for high-throughput screening of small molecule libraries to identify or validate novel modulating agents. In one embodiment, the Mule polypeptide consists essentially of a human Mule BH3 domain peptide.

When agent-biased binding is specifically detected in a solid phase binding or co-immunoprecipitation assays, the modulating agent is typically further validated in an apoptosis assay (e.g. TUNEL and caspase activity assays, etc.) or ubiquitination assay wherein a reduction or increase in apoptosis or ubiquitination, respectively, caused by the agent is detected. Animal models of apoptosis may also be used to further validate therapeutic effect of Mcl-1/Mule polypeptide binding modulating agents (see Example 7).

Mcl-1 functions at an early step in apoptosis induced by various death stimuli and serves as a major survival factor. Overexpression of Mcl-1 has been found in a variety of human malignancies, and often correlates with adverse clinical outcome (Zhang et al., 2002). We have found DNA-damaging agents commonly used in the treatment of cancer have a dramatic decrease in ability to induce apoptosis in cells with Mule knocked down (see Example 6). Accordingly, methods of detecting Mule dysfunction or Mule under-expression in cells having inappropriate Mcl-1 regulation and pathology of apoptosis provide useful clinical diagnostic and prognostic tools, and inform the medical practitioner of appropriate treatment alternatives. In one aspect, the invention provides a diagnostic/prognostic method of characterizing a cancer cell of a patient. The method comprises the step of: determining Mule expression in a cancer cell from the patient, wherein reduced or non-reduced Mule expression relative to that of a control cell indicates that the cancer cell is resistant to or amendable to, respectively, a Mule-dependent therapy; and correspondingly characterizing the cancer cell as resistant to or amenable to a Mule-dependent therapy. Whether a particular cancer therapy is Mule-dependent can be readily ascertained using cell-based assays to determine whether the therapy is able to inhibit proliferation of a cell having reduced Mule expression (see Example 6). In a particular embodiment, the Mule dependent therapy is a DNA damaging therapy such as UV-irradiation, etoposide, cisplatin, etc. A patient diagnosed as having a cancer that is resistant to a Mule-dependent therapy, may be prescribed an alternative therapy such as a cell-cycle inhibitor, an anti-angiogenic treatment, etc.

Mule expression in patient cancer cells can be specifically detected by any of a variety of methods known in the art for detecting gene or protein expression. In one embodiment, the method comprises contacting a fraction of the cancer cell with a Mule-specific binding reagent selected from a Mcl-1 polypeptide or antibody that specifically binds Mule, and measuring specific binding of the reagent to Mule. When a Mule-specific binding reagent is used, the method may also comprise isolating and immobilizing Mule. For example, the Mule may be electrophoretically-separated and blot-transferred for detection by Western Blot, or isolated and solid-phase substrate-bound for detection by labeled immunosorbant assay (e.g. ELISA). In another embodiment, Mule expression in a patient cancer is determined by contacting a fraction of the cancer cell with a Mule mRNA sequence specific probe; and measuring specific hybridization of the probe to Mule mRNA or corresponding cDNA, to provide an indication of Mule expression in the cancer cell.

In another method, reduced Mule expression in a cancer cell is specifically detected by contacting a fraction of the cell with a Mule-specific binding reagent; and detecting a reduction in reagent-bound Mule relative to a control, wherein a reduction in reagent-bound Mule relative to control indicates that the cell has reduced Mule expression, wherein the reagent is selected from a Mcl-1 polypeptide or antibody that specifically binds Mule. In one embodiment, the method further comprises a step of contraindicating a Mule-dependent therapy, wherein the Mule dependent therapy is a DNA damaging therapy selected from the group consisting of UV-irradiation, etoposide and cisplatin.

In another diagnostic/prognostic method, a Mule allele is identified as being associated with increased risk of a disease or disorder of pathological apoptosis, the method comprising the step of detecting the presence of a same Mule allele in a plurality of persons with a disease or disorder of pathological apoptosis, wherein the selective presence of the allele in these persons identifies the allele as being associated with increased risk of a disease or disorder of pathological apoptosis. In certain embodiments, the disease or disorder is a cancer, autoimmune disease, or neurodegenerative disease known to be associated with inappropriate apoptosis regulation. In one embodiment, the disease or disorder is a malignancy characterized by overexpression of Mcl-1. In another embodiment, the disease or disorder is a cisplatin-resistant cancer.

The invention also provides methods of modulating Mcl-1-mediated apoptosis in a cell by contacting the cell with an agent that specifically inhibits or promotes Mcl-1-Mule interaction. In one embodiment, the method comprises inhibiting Mule interaction with Mcl-1 in a Mule- and Mcl-1-expressing cell, by reducing functional expression of Mule or blocking the interaction of Mule and the Mcl-1 in the cell by contacting the cell with a Mule-specific reagent. Applicable Mule-specific reagents that reduce Mule functional expression include Mule-specific siRNA, PNA, morpholino, antisense RNA, etc. Mule-specific reagents that inhibit Mcl-1-Mule protein interaction include, inter alia, a Mule BH3 peptide or peptide mimetic, intrabodies specific to the Mule BH3 domain, and small molecule modulators identified in the disclosed assays that bind Mule and or a Mule/Bcl-1 protein complex and reduce Mcl-1-Mule binding. Additional reagents include specific inhibitors of Mcl-1 ubiquitination, such as are characterized in the disclosed Mcl-1 ubiquitination assays. In one embodiment, the cell is in a patient, and the method comprises an antecedent step of detecting in the patient a pathology of apoptosis. In another embodiment, the method comprises a subsequent step of detecting in the cell a resultant inhibition of Mcl-1-mediated apoptosis. Applicable protocols for contacting the cell with an agent that modulates Mcl-1-Mule interaction are known in the art and routinely optimized. For example, for target cells in vitro or in situ, known lentiviral and retroviral delivery methods can be used to deliver antisense agents, intrabodies, and inhibitory Mule BH3 peptides (see Example 7). In addition, protocols currently used for administration of therapeutics in the treatment of pathologies associated with inappropriate activation or inactivation of apoptosis may be adapted to administer agents that modulate Mcl-1-Mule interaction.

EXAMPLE 1

Mapping Mcl-1 Ubiquitination Sites

Proteins targeted for proteasome degradation are usually modified by a poly-ubiquitin chain (Hershko and Ciechanover, 1998). To test whether Mcl-1 is ubiquitinated, we treated Hela cells with a proteasome inhibitor MG132 to block the proteasome activity and performed western blotting analysis for Mcl-1 to test for the accumulation of higher molecular weight forms that could be ubiquitin modified. Higher molecular weight protein bands were detected by an anti-Mcl-1 antibody in the presence of MG132. This result suggested that polyubiquitination of Mcl-1 might occur. To verify these higher molecular weight bands were indeed caused by polyubiquitin conjugation of Mcl-1, the protein was immunoprecipitated by an anti-Mcl-1 antibody and the immuno-precipitate was probed by an anti-ubiquitin antibody. These higher molecular bands of Mcl-1 could also be recognized by an anti-ubiquitin antibody, indicating that Mcl-1 was polyubiquitinated.

We then established an in vitro ubiquitination assay for Mcl-1. The system comprises an ATP regenerating system, GST-ubiquitin or methylated ubiquitin (ubiquitin was reductively methylated to prevent polyubiquitination chain formation as described by Carrano et al., 1999), ubiquitin aldehyde to block the de-ubiquitin enzymes, radio-labeled recombinant human Mcl-1 protein generated by in vitro translation, and an S100 fraction from HeLa cells. Both GST-ubiquitin and methylated ubiquitin were readily conjugated to the radio labeled Mcl-1. Furthermore, each component was indispensable for this ubiquitin ligating activity.

This in vitro ubiquitination assay with methylated ubiquitin provided us a tool to map the Mcl-1 ubiquitination sites. In principle, methylated ubiquitin cannot be polymerized, therefore, each shifted band with the addition of 7 kDa molecular mass is caused by ubiquitination on a single site. If ubiquitin is present, excess amount of methylated ubiquitin can block polyubiquitin chain formation, resulting in the formation of short polyubiquitin chains. Since Mcl-1 was synthesized in vitro in reticulocyte lysates and an S100 was utilized as a source for ubiquitin ligase activity, polyubiquitin chains derived from ubiquitin present in the reticulocyte lysates or the S100 were terminated by methylated ubiquitin, producing short polyubiquitin chains (mono, di, tri-ubiquitin).

We used this assay in combination with site-specific mutagenesis to examine which lysine residue(s) is required for Mcl-1 ubiquitination. Mcl-1 contains total of 13 lysine residues and could be ubiquitinated to multiple major up-shifted bands with a ~7-kDa interval with methylated ubiquitin in the HeLa S100. None of these ubiquitinated bands was formed when all the lysine residues in Mcl-1 were mutated to arginines.

When the first three lysine residues (5, 40, and 136) were mutated, the majority of Mcl-1 ubiquitination was eliminated and only one major band remained. Among these three lysines, if lysine 136 was intact, a strong short polyubiquitin chain was formed, indicating that lysine 136 was one major ubiquitin target site. The short polyubiquitin chain ligated to lysine 136 disappeared when lysine 136 was mutated, and another short polyubiquitin chain appeared. This chain could be ligated to either lysine 5 or 40, since ablation of both sites blocked its formation but not when either one of them was mutated.

To search for additional sites beyond first three lysines, we combined mutations at the first three lysines with five lysine resides in the middle of Mcl-1 and this change completely abolished Mcl-1 ubiquitination. In contrast, combining the aforementioned mutations with mutations in the last five lysine residues showed the same ubiquitination pattern as the first three lysine mutant alone, indicating that they did not contribute to Mcl-1 ubiquitination. Among the five lysine residues in the middle of Mcl-1, mutations at lysine 194 and 197 in combination with the first three lysine mutants abolished ubiquitination, while the mutations at the lysine residues 208 and 234 did not have much effect. Therefore, five lysine residues (5, 40, 136, 194, and 197) in Mcl-1 protein are involved in ubiquitin conjugation. Consequently, mutations in these five lysine residues lead to prolongation of Mcl-1 half-life. Among these five lysine residues, lysines 136, 194, and 197 are conserved among human, mouse, and rat.

EXAMPLE 2

Mcl-1 Ubiquitination Activity

To isolate the enzyme that carries out Mcl-1 ubiquitination, we fractionated HeLa cell S-100 extracts using the methods described below and reconstituted the Mcl-1 ubiquitination reaction using different column fractions.

In vitro Ubiguitination assay: In 15 ul reaction, 200 ng of recombinant Flag-Mcl-1 is incubated with an ATP regenerating system (50 mM Tris pH 7.6, 5 mM $MgCl_2$, 2 mM ATP, 10 mM creatine phosphate, 3.5 U/ml of creatine kinase), 10 µg of Methyl-Ubiquitin, 10 ng human E1, 100 ng Ubch7, 2 µM of ubiquitin aldehyde, and 10 µg of S100 or designated fractions, at 37° C. for one hour. After terminating the reactions with SDS sample buffer, reaction products were fractionated by SDS-PAGE (10%) and analyzed by western blotting with anti-Flag M2 antibody during purification and anti-Mcl-1 when purified components were used.

We fractionated HeLa S100 through an ion exchange Q column into four fractions: flow through (QFT), proteins bound to the column and eluted at 150 mM NaCl (Q15); proteins bound to the column that were eluted at 300 mM NaCl (Q30), and proteins that bound to the column and were eluted at 1M NaCl (Q100). Three fractions, QFT, Q30, and Q100 were necessary and sufficient to catalyze the Mcl-1 ubiquitination in this reaction. Using a similar ion exchange column, it was reported that majority of E2 activity is present in the QFT, while the E1 resides in the Q30 fraction (Hershko et al., 1983). We therefore substituted Q30 activity with the purified human E1 enzyme and the QFT fraction with several purified recombinant human E2s. We found that the recombinant human E1 could indeed substitute for the Q30 fraction, and one of the E2 enzymes, UbcH7, could substitute the QFT fraction. However, E1 and UbcH7 were not sufficient for the Mcl-1 ubiquitin ligase activity. Addition of the Q100 fraction, rather than QFT, Q15, or Q30, to the reaction containing E1 and UbcH7, restored Mcl-1 ubiquitin ligase activity, indicating that the Q100 fraction contained an E3 enzyme for Mcl-1 ubiquitination. We referred to this Mcl-1 ubiquitin E3 ligase activity present in the Q100 fraction Mule for Mcl-1 ubiquitin ligase E3.

EXAMPLE 3

Biochemical Purification, Molecular Cloning and Recombinant Activity of Mule Using the above-described Mcl-1 ubiquitination as an assay, we purified the Mule activity from the Q100 fraction to apparent homogeneity using column chromatography. The active purified protein fractions were subjected to SDS-PAGE followed by Colloidal blue staining. A protein band with a molecular mass much larger than the highest molecular weight standard used (207 kDA) correlated with the Mcl-1 ligase activity.

To obtain the sequence identity of this Mcl-1 ubiquitin ligase activity, the protein was excised from the gel and subjected to tryptic digestion followed by mass-spectral analysis. The mass fingerprinting of the digested peptides was initially mapped to a previously reported protein Ureb1, a 310 amino acid HECT domain containing protein (Gu et al., 1994). But it was quite apparent that Ureb1 did not represent Mule in its entity because of the size difference. We subsequently performed several rounds of BLAST searching using the NCBI genebank and TIGR human gene index in combination with a Genome Scan using the human genomic sequence to assemble the full length Mule sequence. The finally assembled Mule sequence based on these resources is 4374 amino acid residues long. Furthermore, the peptides we identified with Mass Spectrometry technology using the purified endogenous Mule were matched throughout the newly assembled full-length Mule, including the new N-terminus.

EXAMPLE 4

Recombinant Activity of Mule

After cloning of the full-length Mule, we generated and purified recombinant Mule protein using a baculovirus-based expression system.

The cDNA of full-length human Mule was subcloned into Sal I and Not I sites of pFastBac-1 (Invitrogen). Mule expression baculovirus were prepared according to manufacture's manual (Bac-to-Bac Baculovirus expression system, Invitrogen, Carlsbad, Calif.). Insect cells Sf21 were infected with the P3 virus. The cells were harvested after 2 days of infection. Cell pellet was re-suspended in buffer A and homogenized with a glass douncer (pellet of 1 L culture of infected Sf21 cells was resuspended in 50 ml of buffer A). The homogenate was centrifuged at 100,000 g (SW28 rotor, 25,000 rpm) for 1 hr. The S100 (2 g total protein) were filtered and loaded onto Q column (hand-packed 36 ml of Q Sepharose XL beads). The column was washed with 5 volumes of 100 mM NaCl in buffer A. Then 500 mM NaCl was used to bump the protein out (collecting at 30 ml/tube, measure protein concentration and pooled the high concentration fractions together). The sample above was dialyzed against buffer A and loaded onto 20 ml HiTrap Q XL column (4×5 ml). After loading and washing with 150 mM NaCl, Mule was eluted with a gradient from 150 mM NaCl to 500 mM NaCl. The fractions eluted between 360 and 450 mM NaCl were pooled together and dialyzed against buffer A. The sample was loaded onto 10 ml HiTrap Heparin column. The eluted fractions with NaCl between 280 mM and 450 mM were pooled together and dialyzed against Nickel beads binding buffer (20 mM NaPO4, 500 mM NaCl, pH7.4). The sample was loaded onto 1 ml HisTrap column, washed with 10 mM immidazol and bumped out with 250 mM immidazol. The sample was added with 4 volumes of buffer A and loaded onto 1 ml HiTrap Q column. Western blotting and Coomassie blue staining were used to check Mule in each fraction.

In the presence of E1, Ubch7 (E2), and an ATP regenerating system, the purified recombinant Mule was able to stimulate Mcl-1 ubiquitination with ubiquitin or methylated or GST-tagged ubiquitin but not with an ubiquitin-like protein SUMO. We used methylated ubiquitin for further biochemical analysis because it gave clearer signal. Mule ubiquitinated Mcl-1 in a dose-dependent manner, and the ubiquitination activity relied on the presence of E1 and E2.

The members of Bcl-2 family of proteins containing only the BH3 domain use this domain to interact with other family members. If Mule also uses its BH3 domain to interact with Mcl-1, a peptide containing this domain should compete for Mule-Mcl-1 interaction therefore blocking Mcl-1 ubiquitination in the reconstituted system. To test this hypothesis, we synthesized a 26 amino acid Mule BH3-containing peptide and a mutant peptide in which four hydrophobic residues required for protein-protein interaction were switched with glutamines (4E). The Mule BH3 peptide can efficiently block Mcl-1 ubiquitination at 4 μM, while Mule BH3-4E mutant has no obvious effect even at 20 μM.

EXAMPLE 5

Characterization of Interaction Between Mule and Mcl-1

We generated a monoclonal antibody against the bacterially expressed Mule (amino acids 2219-2396) and performed Western blotting and immunoprecipitation experiments with this antibody. This antibody specifically recognizes the 482 kDa band in human cell extracts. The specificity of this antibody was confirmed by either antigen competition or small RNA interference.

Having an antibody that recognizes the endogenous protein allowed us to specifically deplete Mule from the HeLa extracts. Depletion of Mule with this anti-Mule monoclonal antibody dramatically compromised Mcl-1 ubiquitination in the extracts, indicating that Mule is the major E3 for Mcl-1 in HeLa cell extracts. In contrast, the same depletion experiment performed with another monoclonal antibody against β-tubulin did not deplete Mcl-1 ubiquitin ligase activity.

We next tested whether Mule interacts with Mcl-1 in vivo. Cell extracts from Flag-Mcl-1 expressing cells were immunoprecipitated with an anti-Flag monoclonal antibody. The immunoprecipitates were then subjected to SDS-PAGE and immunoblotted with antibodies against Flag or Mule. The antibody against Flag precipitated Flag-Mcl-1 in Flag-Mcl-1 expressing cells but not in the control cells. The Flag antibody also precipitated Mule, and the amount of co-precipitated Mcl-1 and Mule increased upon treatment with the proteasome inhibitor MG132. These results indicate that Mcl-1 interacts with Mule in vivo.

To examine whether BH3 domain of Mule is sufficient for interaction with Mcl-1, we used a biotin-labeled version of the 26 amino acids Mule BH3 peptide (aa 1969-1994) and the 4E mutant to pull down proteins from cell extracts. Mule BH3 domain specifically pulled down Mcl-1 but not Bcl-xL, Bcl-2, and Bax in HeLa S100, while no interaction between Mule BH3-4E mutant with Mcl-1 was detected. In contrast, the BH3 peptide from another pro-apoptotic BH3-only containing protein Bim was able to pulled down all four proteins as reported before (Harada et al., 2004; Chen et al., 2005).

EXAMPLE 6 siRNA Inhibition of Mule and Effects on Mcl-1 Degradation and Apoptosis

To confirm that Mule was responsible for Mcl-1 degradation in vivo, we eliminated Mule expression by a RNA interference approach targeting the following sequences of human Mule: nt 9931-9949, nt1301-1319, nt 1826-1844, and nt 2206-2224. Transient expression of each of four different siRNAs against Mule was able to eliminate the majority of Mule.

We also established a stable cell line that only expressed small hairpin RNA (shRNA) against Mule upon addition of tetracycline. Mule shRNA sequence si5635 (targeting Mule nt5635-5653) were annealed following the protocol from Oligoengine and cloned into BglII and HindIII sites of pSuperior.puro vector (Oligoengine). The histone H1 promoter and shRNA was released from pSuperior.puro.shRNA construct and subcloned into pBluescript (modified) at sites of EcoRI and HindIII. H1 promoter and shRNA were released from the pBluescript Mule shRNA constructs at the sites of BamHI and BglII, and reinserted into the pBluescript Mule shRNA vector linearized with BglII to generate multiple copies of H1+shRNA cassette. This cloning strategy was repeated several rounds until 7 tandem cassettes were inserted into the same vector. These seven cassettes were then cloned into BamHI site of the pSuperior.puro vector (modified without H1 promoter).

The Mule shRNA construct was co-transfected with tetracycline repressor expression construct into 5×105 attached U2OS cells grown in DMEM with 10% FBS using Lipofectamine transfection reagent (Invitrogen) according to the manufacturer's protocol. One day later, the cells were selected against 1 μg/ml blasticidine and 2 μg/ml puromycin. After two weeks, individual clones were lifted and tested for expression of tetracycline repressor. Positive clones were further tested for Mule shRNA expression. Clones were treated with 2 μg/ml tetracycline for 3 days. Cell extracts were collected and subjected to 6% SDS-PAGE and western blotting with anti-Mule monoclonal antibody. Clones with the best inducible knock down of Mule were chosen for further experiments. This inducible shRNA approach provides superior knockdown efficiency and broadened the time window to evaluate the cellular effect on Mule depletion.

Mule expression was eliminated by tetracycline in a time dependent fashion. After induction with tetracycline for three days, Mule levels became completely undetectable. At the same time, Mcl-1 gradually accumulated and its level of increase correlated well with diminishing Mule. In contrast to Mcl-1, the levels of other Bcl-2 family of proteins including Bcl-xL, Bcl-2, Bax, Bak, Bim, Bid and a control protein actin did not change upon elimination of Mule, a result that was consistent with the specificity of Mule BH3 domain for Mcl-1. We then treated cells with their Mule level knocked down with several DNA damaging agents including UV-irradiation and two commonly used chemotherapeutic drugs etoposide and cisplatin. Cell death induced by all three agents was reduced when Mule was knocked down. The cell death was correlated well with the caspase-3-like (DEVD) activity. Among these DNA damaging agents, cisplatin showed the least ability to induce apoptosis when Mule was knocked down. We therefore performed a detailed biochemical analysis in cells treated with this drug with or without Mule knocked down. In cells that Mule was there, we started to observe caspase-3 activation as measured by its cleavage into active form 4 hours after cisplatin treatment and it continued to increase up to 8 hours. While in cells that Mule was knocked down, we did not see any caspase-3 activation even 6 hours after cisplatin treatment. Only after 8 hours, we started to see weak caspase-3 activation. Consistently, the cleavage of endogenous caspase-3 substrate Poly(ADP-ribose) polymerase, PARP, showed the same pattern.

To test whether the delayed apoptosis when Mule was knocked down has a long last effect, cells were switched to fresh medium after 6 hours of cisplatin treatment and continued culture for 8 days. There were few if any colonies grown up after cells containing Mule were treated with cisplatin. In contrast, there were more than nine fold more colonies that appeared after the same treatment after Mule was knocked down.

EXAMPLE 7

Protective Effect of BH3 Peptide Against Chronic Postischemic Heart Failure

Apoptosis secondary to acute ischemia and chronic remodeling is implicated as a mediator of heart failure. This study was designed using methodology adapted from Chatterjee et al, 2002, to assess the effect of in vivo viral gene transfer of a Mule BH3 domain peptide (BH3 peptide) to block apoptosis and preserve ventricular geometry and function.

The study is performed in accordance with standard animal care and use committee guidelines. A replication-deficient (E1, E3 deleted) adenoviral vector containing a transgene encoding a BH3 peptide (aa 1-1994) and the constitutively active cytomegalovirus (CMV) promoter is obtained.

Thirty New Zealand White rabbits (3 to 4 kg) are used in the study. All rabbits are fully anesthetized with intramuscular doses of ketamine (40 mg/kg), xylazine (2.5 mg/kg), glycopyrrolate (0.02 mg/kg), and buprenorphine (0.05 mg/kg) and then mechanically ventilated (Hallowell EMC model 2000). The left hemithorax is opened through the third intercostal space, exposing the base of the heart. The circumflex artery is identified, and a 6-0 polypropylene suture is placed around its circumference at a point halfway between the atrioventricular groove and the left ventricular (LV) apex. The circumflex tourniquet is tightened to achieve complete cessation of flow as demonstrated by both electrocardiographic changes and visual blanching of the myocardium. After 30 minutes, the tourniquet is released, allowing for reperfusion.

Next, the main pulmonary artery and ascending aorta are each dissected free and encircled with a 0-0 silk suture. Each silk tie is passed through a 14F red rubber catheter creating a tourniquet. The pulmonary tourniquet is then tightened for complete pulmonary artery occlusion. The LV is allowed to empty for 5 seconds, and then the aortic tourniquet is tightened to achieve complete aortic occlusion. A solution (1000 µL) containing $5.0 \times 10^{10}$ particle forming units of recombinant human adeno-CMV-BH3, suspended in 10% glycerol, is injected into the LV cavity in the experimental group (n=11). The control group (n=7) receives 1000 µL of a solution containing $5.0 \times 10^{10}$ particle-forming units of empty vector adeno-null. After 30 seconds of complete outflow occlusion, the tourniquets are removed. The chest is closed, and the animals recover without operative intervention for 6 weeks. During this interval, the animal is studied with transthoracic echocardiography at 2-week intervals (weeks 2, 4, and 6).

The animals return for nonsurvival surgery after 6 weeks. A repeated left thoracotomy is performed with exposure of the LV free wall. A polypropylene suture that marked the site of circumflex artery occlusion identifies the border zone. Four 1-mm piezoelectric sonomicrocrystals are implanted into the myocardium to measure fractional shortening. This includes the placement of 2 crystals in the infarcted region and 2 crystals in the normal LV away from the infarcted region. After sonomicrometry, the heart is arrested in diastole by an intravenous injection of 1 mL KCl (1 mEq/mL), and the right atrium is incised to allow drainage of blood. The heart is procured, and the LV cavity is filled with OCT embedding compound retrograde through the transected aortic root at a constant intracavitary pressure. The catheter is removed and the aortic root is ligated. The heart is placed in a container of OCT embedding compound, bathed in isopentane, frozen in liquid nitrogen, and stored at −80° C.

An additional group of 6 rabbits (n=2, BH3; n=3, adeno-null) undergo the identical surgical procedure but are killed on postoperative day 3 after sononicrometry and echocardiography. The heart is arrested in diastole with 1 mL of KCl (1 mEq/1 mL) and procured as previously described. This group is used to determine whether dnMule administration would demonstrate an effect immediately within 3 days or whether it would be apparent over time. In addition, a group of normal rabbits (n=5) is killed without intervention to determine baseline ventricular wall thickness and diameter. Functional analysis is studied by transthoracic echocardiography to evaluate global cardiac function. Each animal undergoes echocardiography at 2, 4, and 6 weeks after surgery under light sedation (ketamine/xylazine). The group that is killed after 3 days undergo echocardiography before euthanasia. Five normal rabbits are studied to determine baseline ejection fraction (EF). Each of the investigators and an echocardiography specialist are blinded to the treatment group.

Sonomicrometry, a well-established technique that measures LV segmental length changes during each cardiac cycle, is used to measure regional contractility. Contractility across the border zone is measured between a crystal in the infarcted region and the ipsilateral (in relation to the tourniquet site of occlusion) crystal 10 mm apart in the viable myocardium. Normal contractility is measured between the 2 crystals in the viable myocardium. Fractional shortening is defined as the difference between the end-diastolic length and the end-systolic length divided by the end-diastolic length (the distance between the crystals). The data are analyzed with Sonoview software (Sonometrics Corp.) and reported as a percentage of baseline ±SEM.

Four sections from each heart are analyzed for infarct percentage of the LV by triphenyl tetrazolium chloride (TTC) incubation. Images of both pre-TTC- and post-TTC incubation hearts are scanned into Adobe Photoshop. The area that is not stained by TTC is measured and calculated as the infarct area. Infarct percentage size for each heart is defined as (infarct area of each slice/total area of LV)×100.

In both groups, 4 adjacent sections, midway between the base and the apex spanning the border zone and perpendicular to the longitudinal axis of the ventricle, are obtained to measure chamber diameter and thickness of the free wall of the ventricle. Five equally spaced measurements of the free wall of the LV are collected from each slice, and the values are averaged by each of 2 investigators blinded to the treatment groups. Measurements are obtained with a dissecting microscope with a micrometer accurate to 0.03 mm. Five native rabbits are also killed to evaluate the chamber diameters and wall thickness in uninfarcted and untreated animals.

Specimens are obtained from storage in a −80° C. freezer and allowed to warm to approximately 22° C. Five transverse 10-µm sections of the border zone are prepared with a cryostat at 0.25-cm intervals from the point of circumflex occlusion to the apex of the heart. Terminal deoxynucleotidyl transferase-mediated dUTP nickend labeling (TUNEL) assay is performed with a TdT-FragEL DNA fragmentation detection kit (Oncogene Research Products). The apoptotic index is taken as the number of apoptotic nuclei per high-powered field (HPF) examined in 5 measurements obtained from the free wall of each section, by each of 2 investigators blinded to the treatment group. The apoptotic index is expressed as a percentage of the number of apoptotic cells per total nuclei in each HPF examined.

Specimens obtained for Western blotting are snap-frozen in liquid nitrogen after removal from the animal, without OCT fixative. Specimens are pulverized, homogenized in 10 volumes of sodium dodecyl sulfate (SDS) lysis buffer (100 mmol/L Tris, pH 8.0; 10% SDS, 10 mmol/L EDTA, 50 mmol/L dithiothreitol), and sheared with a 25-gauge needle. Samples are normalized for total protein content, and 50 µg of each sample is electrophoresed on a 12.5% SDS-polyacrylamide gel after addition of 6× sample loading buffer and 3 minutes of denaturation at 100° C. Proteins are then transferred to Immobilon-P (Millipore) by using a wet transfer apparatus. The membrane is subsequently blocked with 5% nonfat dry milk in Tris-buffered saline containing 0.05% Tween-20. Immunoblotting is performed using a mouse monoclonal antibody against human Mule BH3 peptide. Detection is performed using the ECL kit (Amersham). Subsequently, the Immobilon-P membrane is stained with Coomassie blue, and the actin band is identified to confirm equal loading conditions.

At 6 weeks, increased expression of Mule BH3 peptide is demonstrated in the adeno-BH3-treated group compared with controls. In Mule BH3-treated animals compared to controls, an echocardiography maintaining higher EF and sonomicrometry showing greater preservation of fractional shortening demonstrate a greater preservation of myocardial contractility. Control rabbits have significant ventricular dilatation with a greater mean LV midchamber diameter compared with uninfarcted and untreated native rabbits. There is significant wall thinning in the control group compared with native rabbits. In contrast, preservation of ventricular geometry in rabbits treated with adeno-BH3 is evidenced by a lack of statistically significant difference from native rabbits with respect to ventricular diameter or mean free-wall thickness, along with a significant preservation of chamber dilatation and free-wall thickness, and a significant reduction in the apoptotic index compared with controls.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims

REFERENCES

Aravind, L. (2001). Trends Biochem Sci 26:273-275.
Carrano, et al. (1999). Nat Cell Biol 1:193-199.
Chatterjee et al. (2002) Circulation. 106[suppl I]:I-212-I-217.
Chen, L., et al (2005). Mol Cell 17:393-403.
Cuconati, A., et al (2003). Genes Dev 17:2922-2932.
Danial, N. N., and Korsmeyer, S. J. (2004). Cell 116:205-219.
Derouet, M., et al (2004). J Biol Chem 279:26915-26921.
Du, C., et al (2000). Cell 102:33-42.
Gross, A., et al. (1999). Genes Dev 13:1899-1911.
Gu, J., et al (1994). Brain Res Mol Brain Res 24:77-88.
Harada, H., et al (2004). Proc Natl Acad Sci USA 101: 15313-15317.
Hershko, A., and Ciechanover, A. (1998). Annu Rev Biochem 67:425-479.
Hershko, A., et al (1983). J Biol Chem 258:8206-8214.
Hofmann, K., and Bucher, P. (1996). Trends Biochem Sci 21:172-173.
Huang, H. M., et al (2000). Blood 96:1764-1771.
Kerr, J. F., et al (1972). Br J Cancer 26:239-257.
Kozopas, et al (1993). Proc Natl Acad Sci USA 90:3516-3520.
Le Gouill, et al (2004). Blood 104:2886-2892.
Liu, X., et al (1996). Cell 86:147-157.
Liu et al (2005). Mol. Cell. Biol. 25:2819-2831.
Martinou, J. C., and Green, D. R. (2001). Nat Rev Mol Cell Biol 2:63-67.
Meier P, Silke J, (2003) Nat Cell Biol. 5:1035-1038.
Nencioni, A., et al (2004). Blood 105:3255-3262
Nijhawan, D., et al (2003). Genes Dev 17:1475-1486.
Piret, J. P., et al (2005). J Biol Chem. 280:9336-9344.
Verhagen, A. M., et al (2000). Cell 102:43-53.
Yang, et al (1996). J Cell Physiol 166:523-536.
Yang, T., et al (1995). J Cell Biol 128:1173-1184.
Zhang, B., et al (2002). Blood 99:1885-1893.
Zhou, P., et al (1998). Blood 92:3226-3239.
Zhou, P., et al (1997). Blood 89:630-643.

What is claimed is:

1. A method for identifying an agent that inhibits binding of mammalian Mcl-1 with a human or mouse Mule polypeptide comprising a Mule BH3 domain in a mixture, comprising:
    contacting the mixture with a candidate agent under conditions wherein but for the presence of the agent, the Mcl-1 and Mule polypeptide engage in a reference binding; and
    specifically detecting an agent-biased binding of the Mcl-1 and Mule polypeptide that is different from the reference binding, indicating that the agent is a inhibitor of binding of the Mcl-1 and the Mule polypeptide.

2. The method of claim 1 wherein the Mcl-1 and Mule polypeptide are isolated, recombinantly-expressed, or in a predetermined amount.

3. The method of claim 1 wherein the mixture is within a cell transformed to express the Mcl-1 or the Mule polypeptide.

4. The method of claim 1 wherein the agent-biased specific binding is detected in an in vitro Mcl-1 ubiquitination assay.

5. The method of claim 1 wherein the agent-biased specific binding is detected in a co-immunoprecipitation assay.

6. The method of claim 1 wherein the agent-biased specific binding is detected in a solid phase binding assay.

7. The method of claim 1 wherein the agent-biased specific binding is detected in a solid phase binding assay and the Mule polypeptide consists essentially of a human Mule BH3 domain peptide.

8. The method of claim 1 further comprising a step of testing the agent in an apoptosis assay, and detecting a reduction or increase in apoptosis caused by the agent.

9. The method of claim 1 wherein the agent-biased specific binding is detected in an in vitro Mcl-1 ubiquitination assay wherein the Mule polypeptide is recombinant or part of a cell fraction, and the Mcl-1 is recombinant human Mcl-1, and the assay comprises incubating the Mcl-1 and the Mule polypeptide with an ATP regenerating system, methyl-ubiquitin, recombinant human E1, human E2, and ubiquitin aldehyde, with and without the candidate agent, and wherein resultant reaction products are fractionated in a biochemical or electrophoretic gel based-assay that measures Mcl-1 protein mobility shifts, wherein because functional Mule is specifically required for Mcl-1 ubiquitination, increased or decreased ubiquitination in the presence of the candidate agent provides a specific indication of Mcl-1/Mule polypeptide binding.

10. The method of claim 1 wherein the agent-biased specific binding is detected in an in vitro Mcl-1 ubiquitination assay wherein the Mule polypeptide is recombinant or part of a cell fraction, and the Mcl-1 is recombinant human Mcl-1, and the assay comprises incubating the Mcl-1 and the Mule polypeptide with an ATP regenerating system, methylubiquitin, recombinant human E1, human E2, and ubiquitin aldehyde, with and without the candidate agent, and wherein resultant reaction products are fractionated by mass spectrometry analysis to resolve ubiquitination, wherein because functional Mule is specifically required for Mcl-1 ubiquitination, increased or decreased ubiquitination in the presence of the candidate agent provides a specific indication of Mcl-1/Mule polypeptide binding.

11. The method of claim 1 wherein the agent-biased specific binding is detected in a co-immunoprecipitation assay, wherein the Mcl-1 is Flag-tagged Mcl-1 stably expressed by HeLa cells treated with and without the candidate modulating agent, where after the cells are lysed, resultant cell extracts are immunoprecipitated by anti-Flag mAb, resultant immunoprecipitate is subjected to SDS-PAGE followed by electroblotting to a nitrocellulose filter, and the filter is probed with an anti-Mule antibody and exposed to an X-ray film.

12. The method of claim 1 wherein the agent-biased specific binding is detected in a solid phase binding assay, wherein the Mule polypeptide is bound to a solid-phase, the Mcl-1 is labeled, and the amount of a labeled Mcl-1 that binds to the Mule polypeptide in the presence and absence of the candidate agent is detected.

13. The method of claim 1 wherein the agent-biased specific binding is detected in a solid phase binding assay, wherein the Mule polypeptide is bound to a solid-phase, the Mcl-1 is labeled, and the amount of a labeled Mcl-1 that binds to the Mule polypeptide in the presence and absence of the candidate agent is detected, wherein the Mule polypeptide consists essentially of a human Mule BH3 domain peptide.

14. The method of claim 1 wherein the agent-biased specific binding is detected in a solid phase binding assay, wherein the Mcl-1 is bound to the solid phase, the Mule polypeptide is labeled, and the amount of the labeled Mule polypeptide that binds to the Mcl-1 in the presence and absence of the agent is detected.

15. The method of claim 1 wherein the agent-biased specific binding is detected in a solid phase binding assay, wherein the Mcl-1 is bound to the solid phase, the Mule polypeptide is labeled, and the amount of the labeled Mule polypeptide that binds to the Mcl-1 in the presence and absence of the agent is detected, wherein the Mule polypeptide consists essentially of a human Mule BH3 domain peptide.

16. The method of claim 1 further comprising a step of testing the agent in an apoptosis assay, and detecting a reduction or increase in apoptosis caused by the agent, wherein the apoptosis assay is a TUNEL ((Terminal deoxynucleotidyl Transferase Biotin-dUTP Nick End Labeling) assay.

17. The method of claim 1 further comprising a step of testing the agent in an apoptosis assay, and detecting a reduction or increase in apoptosis caused by the agent, wherein the apoptosis assay is a caspase activity assay.

18. The method of claim 1 further comprising a step of testing the agent in an apoptosis assay, and detecting a reduction or increase in apoptosis caused by the agent, wherein the apoptosis assay is an animal model of apoptosis, wherein the animal model is a rodent model of chronic postischemic heart failure.

* * * * *